United States Patent
Lee et al.

(10) Patent No.: US 7,209,542 B2
(45) Date of Patent: Apr. 24, 2007

(54) SIMULTANEOUS MEASUREMENT OF THE REFLECTIVITY OF X-RAY WITH DIFFERENT ORDERS OF REFLECTIONS AND APPARATUS FOR MEASUREMENT THEREOF

(75) Inventors: Sang Gon Lee, Daejeon (KR); Jun Gyo Bak, Daejeon (KR); Manfred Bitter, Princeton, NJ (US)

(73) Assignee: Korea Basic Science Institute (KR)

( * ) Notice: Subject to any disclaimer, the term of this patent is extended or adjusted under 35 U.S.C. 154(b) by 0 days.

(21) Appl. No.: 11/178,142

(22) Filed: Jul. 8, 2005

(65) Prior Publication Data

US 2006/0126786 A1 Jun. 15, 2006

(30) Foreign Application Priority Data

Dec. 14, 2004 (KR) .............. 10-2004-0105268

(51) Int. Cl.
*G01N 23/20* (2006.01)
*G01N 23/207* (2006.01)
(52) U.S. Cl. .................................. 378/73; 378/70
(58) Field of Classification Search ............ 378/70–82, 378/198
See application file for complete search history.

(56) References Cited

U.S. PATENT DOCUMENTS

| | | | |
|---|---|---|---|
| 4,882,780 A * | 11/1989 | Wittry .................. | 378/84 |
| 5,493,122 A * | 2/1996 | Farr ...................... | 250/370.06 |
| 6,198,796 B1 * | 3/2001 | Yokoyama et al. ........... | 378/73 |
| 6,697,453 B1 * | 2/2004 | Mueller et al. ............... | 378/72 |
| 6,751,287 B1 * | 6/2004 | Kalyon et al. ................ | 378/71 |
| 6,768,785 B2 * | 7/2004 | Koppel et al. ................ | 378/70 |
| 6,986,798 B2 * | 1/2006 | Bessho et al. ................ | 51/307 |
| 6,987,832 B2 * | 1/2006 | Koppel et al. ................ | 378/70 |
| 2002/0126966 A1* | 9/2002 | Hirsch .......................... | 385/95 |
| 2005/0094766 A1* | 5/2005 | Yokhin .......................... | 378/86 |

FOREIGN PATENT DOCUMENTS

JP 09-033451 A 7/1997

OTHER PUBLICATIONS

G. Holzer et al., "Flat and Spherically Bent Muscovite (Mica) Crystals for X-ray Spectroscopy," Physical Scripta, 1998, vol. 57, pp. 301-309.

* cited by examiner

*Primary Examiner*—Edward J. Glick
*Assistant Examiner*—Irakli Kiknadze
(74) *Attorney, Agent, or Firm*—Cantor Colburn LLP

(57) ABSTRACT

Disclosed are an apparatus and a method for simultaneously measuring integrated reflectivity of X-rays with different orders of reflections in crystal. Continuous X-rays are incident into the crystal and reflection intensities of the X-rays reflected from the crystal with different orders of reflections are measured based on Bragg's law, thereby measuring reflectivity of X-rays with different orders of reflections.

9 Claims, 3 Drawing Sheets

SIMULTANEOUS MEASUREMENT OF THE REFLECTIVITY OF X-RAY WITH DIFFERENT ORDERS OF REFLECTIONS AND APPARATUS FOR MEASUREMENT THEREOF

TECHNICAL FIELD

The present invention relates to an apparatus and a method for simultaneously measuring integrated reflectivity of X-rays with different orders of reflections in crystals. More particularly, the present invention relates to a method for simultaneously measuring integrated reflectivity of X-rays with different orders of reflections, in which bremsstrahlung continuum or continuous X-rays are incident into crystal and reflection intensities of the X-rays reflected from the crystal are measured based on Bragg's law, thereby measuring the reflectivity of X-rays with different orders of reflections.

BACKGROUND ART

As generally known in the art, X-rays were first observed and documented in 1895 by Wilhelm Conrad Roentgen, a German scientist. At that time, X-rays were used as a radiograph for detecting an internal structure of an object. In 1912, a German physicist named Laue discovered diffraction of X-rays. That is, X-ray diffractometry was established based on the fact that crystal reflects X-ray irradiated into the crystal if the X-ray has a wavelength corresponding to a plane spacing of the crystal. The X-ray diffractometry demonstrates the wave nature of the X-ray and the regular alignment of atoms in the crystal.

In the same year (1912), a British scientist named Bragg suggested conditions required for the X-ray diffraction by analyzing the X-ray diffractomerty and developed Bragg's law to simply explain X-ray scattering from atomic planes of the crystal.

The X-ray diffractometry is useful for understanding the alignment and relative positions of atoms provided in a substance having a relatively simple structure and physical properties of metals, polymeric materials and solid materials. Recently, the X-ray diffractometry is extensively used for analyzing internal structures of complex natural substances, such as steroid, vitamin, or antibiotic substances.

The X-ray is generated when a charged particle having sufficient energy suddenly stops its movement. In general, the X-ray is created in an X-ray tube having an electron source and two metal electrodes. Since high voltage (tens of thousands of volts) is applied between two metal electrodes, electrons are emitted from a cathode of the electron source due to the high voltage. The electrons may collide with a metal target provided at an anode of the electron source with a high speed, thereby generating the X-ray. Such an X-ray source may create a continuous spectrum and a linear spectrum. Accordingly, the X-rays are classified into continuous X-rays or white X-rays representing the continuous spectrum and characteristic X-rays representing the linear spectrum. The continuous X-rays and characteristic X-rays are very important when analyzing properties of substances.

The continuous X-ray is called "white radiation ray" or "Bremsstrahlung", which is generated when a part of energy of the electrons colliding with the metal target is converted into X-ray photons.

Referring to an X-ray emission spectrum, a smooth curve of the X-ray emission spectrum is suddenly peaked at a predetermined wavelength. An X-ray having a wavelength representing the peak is called a "characteristic X-ray". The wavelength of the characteristic X-ray may vary depending on substances and several characteristic X-rays are observed in the same substance. The wavelength of the characteristic X-ray has a characteristic value, which may vary depending on elements forming a target material, and is classified into various classes, such as K, L, M, etc, according to the energy level of the electrons. At this time, the size of the wavelength is in an order of K<L<M . . . , and several wavelengths may exist in the same class.

An atom consists of a nucleus and an electron moving around the nucleus along an orbit with a predetermined energy level. If kinetic energy of the electron used for generating the X-ray is larger than bonding energy of the electron moving along the orbit with the predetermined energy level, the electron in the predetermined energy level is emitted. In addition, an electron aligned in an outer energy level is excited and moved into an empty space of the predetermined energy level. At this time, the characteristic X-ray is generated in each energy level.

The term "reflectivity" signifies an intensity ratio of reflected light to incident light and is utilized as an index showing the property of substances. Such reflectivity, which represents a reflection degree of light or radiation from a surface of an object, is determined according to the kind and the surface state of substances. In general, metals represent higher reflectivity. For instance, copper has reflectivity of 59% and silver has reflectivity of 95%. If an object is coated with black material, the object represents lower reflectivity due to a higher absorption characteristic of the black material. For example, soot absorbs 95% of light and reflects 5% of light. In addition, the reflectivity relates to the wavelength of incident light.

Crystal is used for reflecting the X-ray. The crystal plays the role of a mirror used for reflecting the visible ray. The reflectivity is one of important characteristics of the crystal. Thus, it is very important to rapidly and precisely measure the reflectivity of the crystal when performing X-ray tests or dealing with X-ray appliances.

Conventionally, the characteristic X-ray is used for measuring the reflectivity of the crystal.

That is, the characteristic X-ray generated from an anode of an X-ray tube is irradiated onto a sample crystal by means of a monochromator, and then reflection intensity of the characteristic X-ray is measured in order to obtain the reflectivity of the crystal. The reflection intensity of the characteristic X-ray reflected from the sample crystal can be obtained by measuring the number of photons using a scintillator, which is an X-ray detector, or a PM tube.

However, in order to allow the characteristic X-ray to be reflected from the surface of the sample crystal, constructive interference must occur between reflective waves in internal and external portions of the sample crystal. For this reason, in order to measure the reflectivity of the sample crystal by using the characteristic X-ray, it is necessary to find a specific incident angle of the characteristic X-ray while adjusting the incident angle of the characteristic X-ray with respect to the sample crystal in such a manner that the constructive interference occurs between reflective waves. In addition, in order to measure reflectivity of the X-rays with different orders of reflections, incident angles (Bragg angles) of the X-rays must be changed whenever they are incident into the crystal while rearranging the total system.

In addition, according to the conventional measurement method, since a cross sectional area of the characteristic X-ray beam irradiated onto the test sample is very small (about 1 mm$^2$), it is necessary to rotate the sample crystal in order to find a spot incurring maximum reflectivity. Furthermore, the conventional measurement method uses the characteristic X-ray for measuring the reflectivity of the sample crystal, so an amount of available X-ray energy is limited. In addition, it is necessary to scan planes of large-sized crystal with the characteristic X-ray by several times in order to measure reflectivity of the large-sized crystal.

SUMMARY OF THE INVENTION

The present invention has been made in order to solve the above-mentioned problems occurring in the prior art. The present invention provides a method for simultaneously measuring integrated reflectivity of X-rays with different orders of reflections by measuring reflection intensities of X-rays reflected from a sample after irradiating continuous X-rays onto the sample. That is, according to the present invention, continuous X-rays are used instead of characteristic X-rays and reflected waves of the continuous X-rays are detected in order to simultaneously measure integrated reflectivity of X-rays with different orders of reflections.

In detail, according to one exemplary embodiment of the present invention, the continuous X-rays are irradiated onto the sample and intensities of the X-rays reflected from the sample are measured by means of a detector having an energy resolution function or a wavelength resolution function, thereby obtaining reflection intensities of the X-rays with different orders of reflections at a predetermined wavelength ($\lambda$) or energy level ($E=hc/\lambda$) causing the reflection. Then, an intensity ratio of the reflected X-ray to the incident X-ray is calculated, thereby simultaneously measuring integrated reflectivity of X-rays with different orders of reflections.

Accordingly, it is an object of the present invention to provide a method of simultaneously measuring reflection intensities of X-rays with different orders of reflections. In addition, it is another object of the present invention to provide a method of simultaneously measuring integrated reflectivity of X-rays with different orders of reflections.

The present invention provides a method for measuring integrated reflectivity of crystal by using continuous X-rays. Thus, according to the present invention, it is not necessary to adjust an incident angle of the X-ray in order to find a Bragg angle that can cause the reflection of the X-ray.

The present invention provides an apparatus for simultaneously measuring reflection intensities of X-rays with different orders of reflections. In addition, the present invention also provides an apparatus for simultaneously measuring integrated reflectivity of X-rays with different orders of reflections.

In detail, according to one exemplary embodiment of the present invention, there is provided an apparatus for simultaneously measuring reflection intensities of X-rays with different orders of reflections including an X-ray tube, a sample-fixing unit and a detector, which are geometrically positioned in a Rowland circle.

In the meantime, the apparatus for simultaneously measuring integrated reflectivity of X-rays with different orders of reflections includes a reflectivity calculator in addition to the above reflection intensity measurement apparatus. The reflectivity calculator detects an intensity ratio of X-rays reflected from the sample to X-rays incident into the sample, thereby calculating the reflectivity of the X-rays.

In the present invention, the term "reflection of X-rays with different orders" signifies reflection of X-rays having various wavelengths satisfying Bragg's law. In addition, the term "simultaneous measurement of integrated reflectivity of X-rays" signifies that reflectivity of various X-rays satisfying Bragg's law is simultaneously measured.

BRIEF DESCRIPTION OF THE DRAWINGS

The foregoing and other objects, features and advantages of the present invention will become more apparent from the following detailed description when taken in conjunction with the accompanying drawings in which.

BRIEF DESCRIPTION OF THE INDICATION NUMBERS IN THE DRAWINGS

1: X-ray generator (X-ray Tube)
2: Rowland circle
3: Sample (Crystal)
4: Detector

DETAILED DESCRIPTION OF THE INVENTION

Hereinafter, the present invention will be described in more detail with reference to accompanying drawings. In addition, reference will now be made in detail to the preferred embodiments of the present invention.

Light incident into a substance is reflected from the substance. Such a phenomenon is called "reflection". In a case of crystal, the reflection may occur according to Bragg's law. Hereinafter, description will be made in relation to the reflection with reference to FIG. 4.

Figure 4:
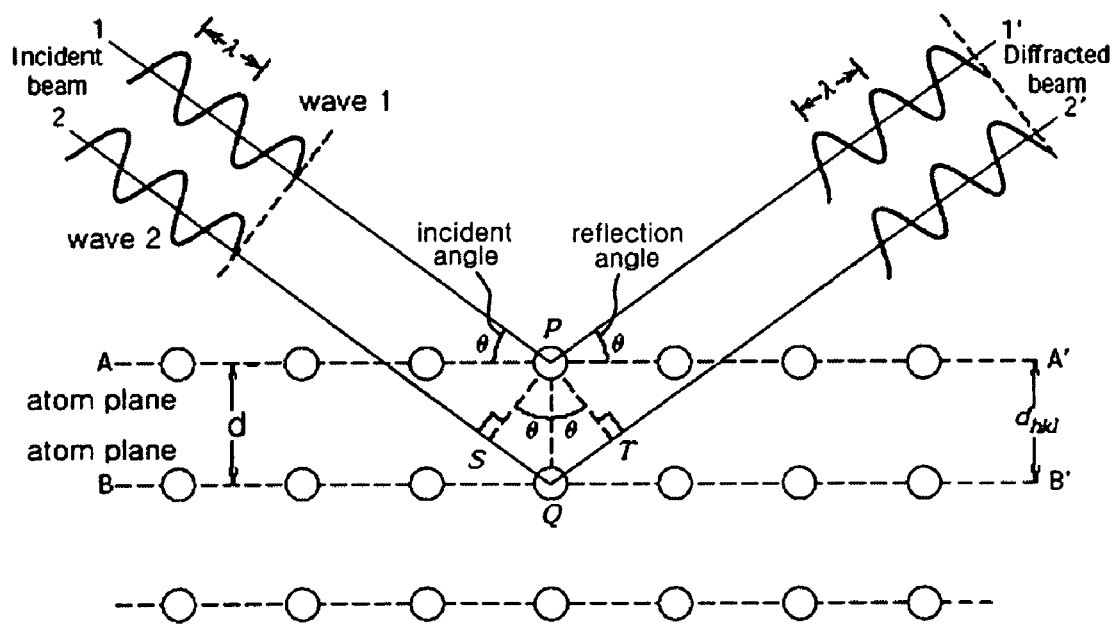
FIG. 4 is a view illustrating a principle of Bragg diffraction.
Figure 5:
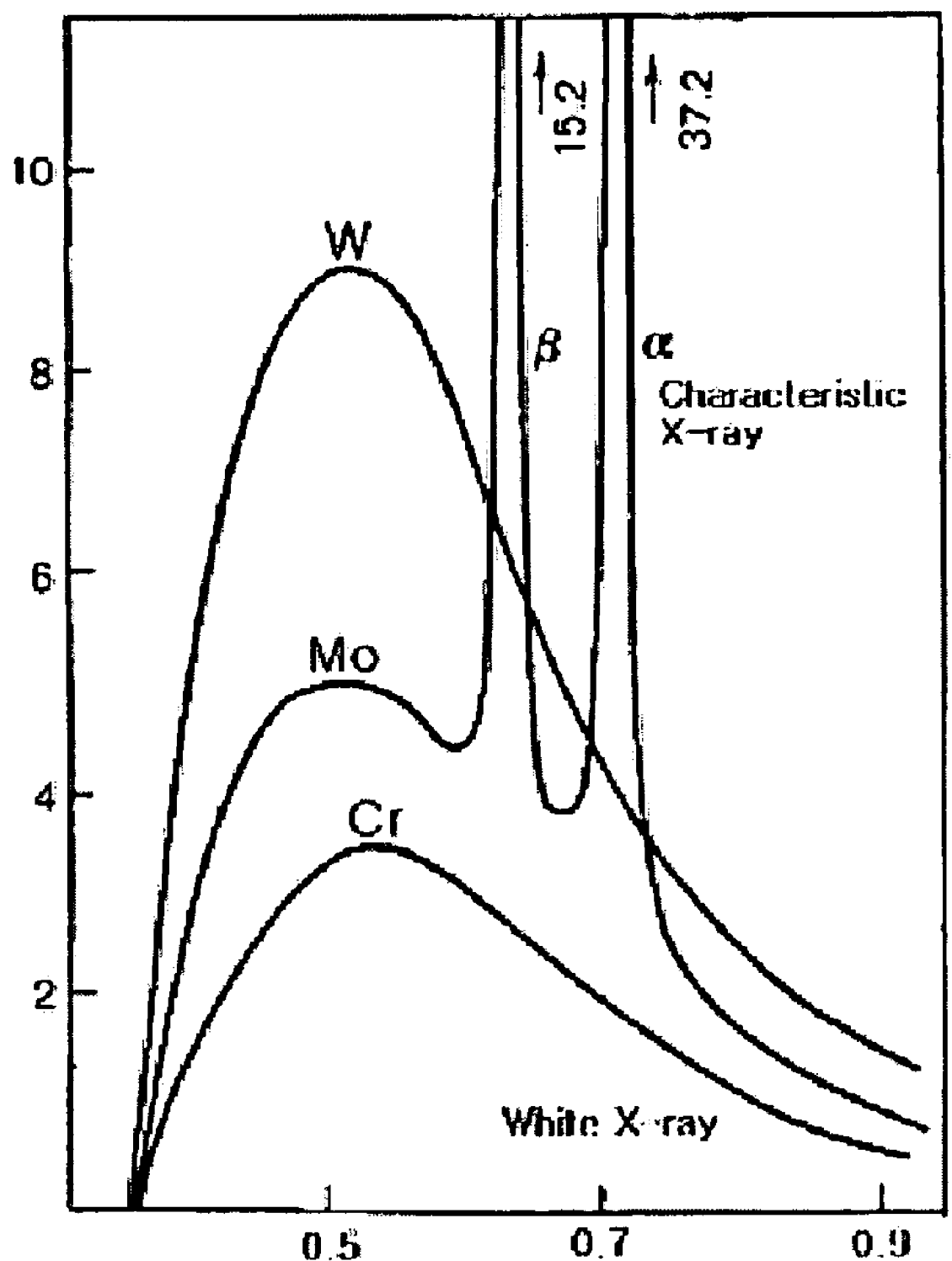
FIG. 5 is a view illustrating an example of X-ray spectrums representing continuous X-rays and characteristic X-rays.

In order to maximize intensity of X-rays reflected from crystal, phases of reflected waves should be identical to each other in such a manner that constructive interference occurs between the reflected waves. That is, predetermined portions of the reflected waves (for example, peaks or bottoms of waves) must simultaneously arrive at the observation place. As shown in FIG. 4, two waves 1 and 2 having the same phase are reflected from atoms A and B provided in the crystal. The plane spacing between lattices (or, atoms) of the crystal is "d". In addition, a reflection angle $\theta$ is identical to an incident angle $\theta$. In order to allow two waves 1 and 2 to maintain the same phase after the two waves 1 and 2 have been reflected from atoms A and B, a path difference (CBD) must be set within an integer range of the wavelength ($\lambda$) (that is, CBD=$n\lambda$, wherein n is integer). Geometrically, a length of CB is identical to a length of BD and the length of CB or BD can be obtained through multiplying the plane spacing "d" of the lattices by the reflection angle $\theta$ (that is, d×sin $\theta$). Thus, an equation $n\lambda = 2d \sin \theta$ called "Bragg's law" is established.

As can be understood from FIG. 4, if n=2, only one wavelength exists in the path CB and a reflection angle of light is smaller than that of a case where n=3. In the meantime, if n is not the integer, the reflected waves are subject to destructive interference so that no wave will emerge. Thus, when the X-rays are reflected from the crystal, the X-rays may be reflected with different orders of reflections depending on the value of n.

The term "reflection with different orders" used in the present invention is derived from the fact that the X-ray has a plurality of reflected waves having various values of n. In addition, according to the present invention, reflectivity of various X-rays satisfying Bragg's law is simultaneously measured, which is called "simultaneous measurement of integrated reflectivity of X-rays". That is, according to the present invention, it is possible to simultaneously measure reflection and reflectivity of X-rays having various wavelengths (that is, various values of n).

Conventionally, the characteristic X-rays are used to measure reflectivity of the crystal. In this case, since the wavelength of the characteristic X-ray has been determined, it is necessary to vary the incident angle θ of the characteristic X-ray in order to find conditions of the crystal causing the reflection. However, the present invention uses the continuous X-rays having various wavelengths. Thus, there are many wavelengths causing the constructive interference even if the incident angle of the continuous X-ray is fixed. That is, since X-rays having various wavelengths are irradiated onto the crystal, reflection may occur due to the constructive interference of the X-rays having various wavelengths.

Figure 2:
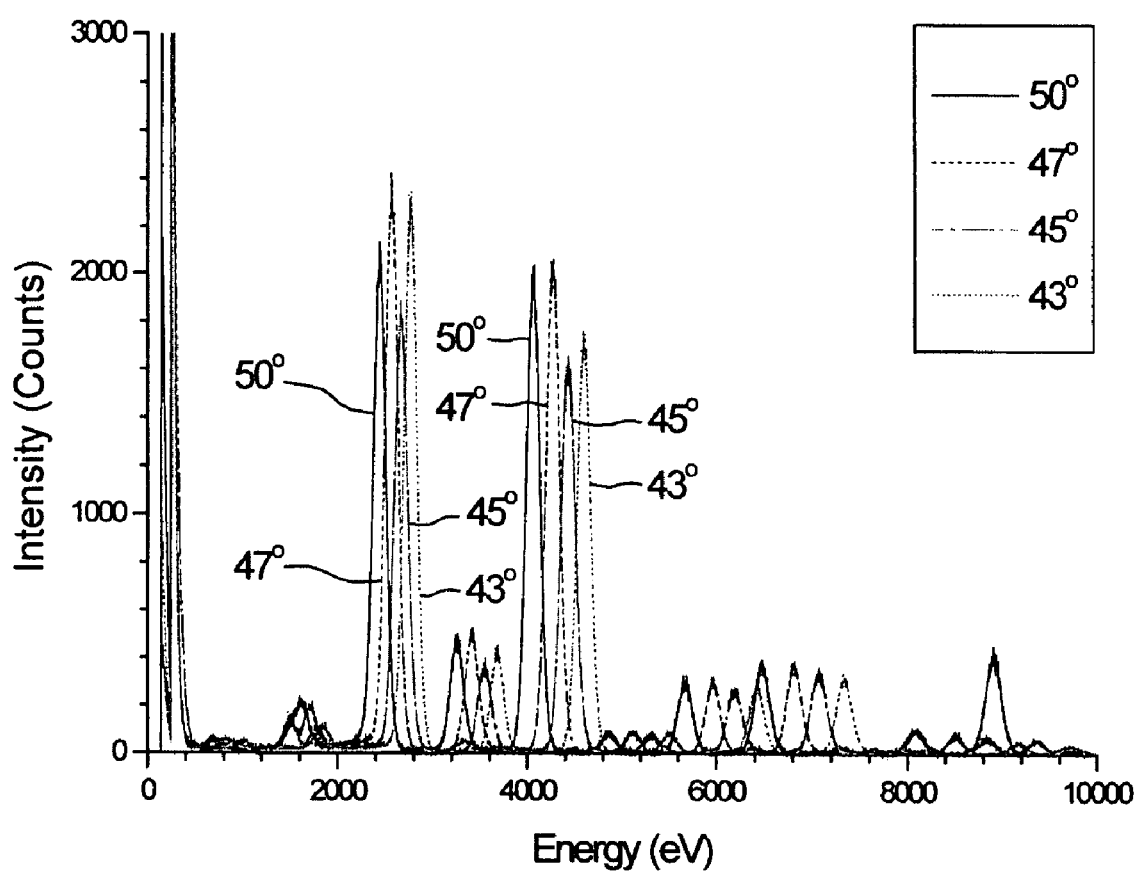
FIG. 2 is a graph illustrating a test result obtained by simultaneously measuring integrated reflectivity of mica crystal when X-rays with different orders of reflections are incident into the mica crystal according to one embodiment of the present invention.

According to the method for measuring reflectivity of the X-ray of the present invention, when intensity of the X-rays reflected from the sample is measured by using a continuous wavelength spectrum or a continuous energy spectrum, the peak of the X-ray is detected at a predetermined wavelength or predetermined energy. Reflection of the X-ray may occur at the peak point. FIG. 2 shows intensity of the reflected wave detected by using the energy spectrum. Referring to FIG. 2, 12 peak points are detected. In this case, 12 energy intensities are measured.

According to Bragg's law (nλ=2d sin θ), n can be represented as follows:

$$n = 2d \sin \theta / \lambda \quad \text{[Equation 1]}$$

As can be understood from Equation 1, the condition causing the reflection can be found even if the incident angle of the X-ray is fixed. If a wavelength range is wide, various integer values of n can be obtained, so the reflections with different orders can be realized.

In cases of multiple reflections, reflected waves having various wavelengths are mixed with each other, so a detector must detect the reflected waves by analyzing the wavelength of each wave. For this reason, a detector capable of analyzing the intensity of the reflected waves through the wavelength spectrum is adaptable for the present invention.

In addition, the wavelength of the wave can be represented as energy as shown in Equation 2. Thus, a detector having an energy resolution function is also adaptable for the present invention.

$$E = hc/\lambda \text{ (wherein, } E\text{: energy, } h\text{: Planck constant, } c\text{: speed of light, and } \lambda\text{: wavelength)} \quad \text{[Equation 2]}$$

If Equation 2 is applied to Bragg's law (nλ=2d sin θ), the condition causing the reflection through the wavelength energy spectrum can be obtained as follows:

$$n = (2d \sin \theta \cdot E)/(hc) \quad \text{[Equation 3]}$$

Therefore, a detector having an energy resolution function can be used in the present invention.

For instance, the detector includes a Si—Li detector or a Si-Pin diode detector. However, the present invention is not limited thereto.

The reflectivity of the X-ray can be obtained by comparing reflection intensity of the X-ray detected from the detector with intensity of the X-ray incident into the sample. Equation 4 shows the reflectivity of the X-ray.

$$\text{Reflectivity} = [\text{reflection intensity } (I_r)/\text{incident intensity } (I_i)] \times 100 \quad \text{[Equation 4]}$$

According to the present invention, the continuous X-rays are irradiated onto the sample and intensity of X-rays reflected from the sample is measured in order to simultaneously measure reflectivity of X-rays with different orders of reflections.

Figure 1:
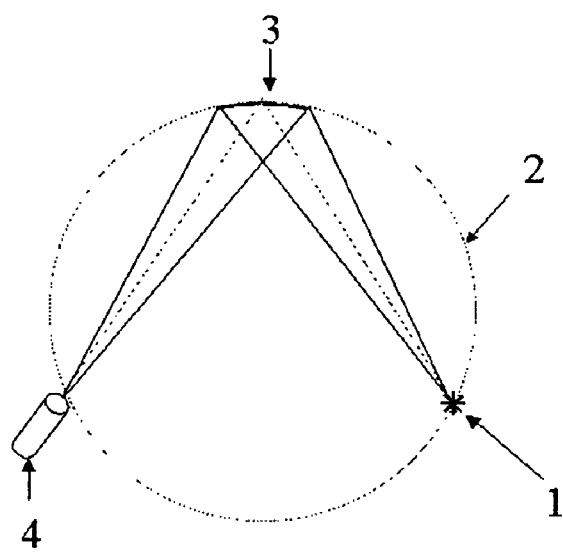
FIG. 1 is a schematic view illustrating a principle of a method for simultaneous measuring integrated reflectivity of X-rays with different orders of reflections according to one embodiment of the present invention.

As shown in FIG. 1, according to the present invention, an X-ray tube, a sample and a detector are preferably aligned in a Rowland circle. In this case, the X-rays can be irradiated over the wide range of the sample, so that the reflectivity of the sample having a relatively large area can be measured at a time.

According to the conventional method, since the characteristic X-ray beam has a very small cross sectional area (about 1 mm$^2$), it is necessary to rotate the sample crystal in order to find a spot incurring maximum reflectivity. However, according to the present invention, the continuous X-rays are directly irradiated onto the test sample and the reflection intensity of the reflected X-rays is continuously observed by using the wavelength spectrum or the energy spectrum. Accordingly, it is possible to simultaneously measure the integrated reflectivity of the X-rays with different orders of reflection at a time.

The present invention does not limit the kind of the X-rays and energy thereof. In addition, since the present invention causes the constructive interference of the X-rays, it is not necessary to adjust the incident angle of the X-rays for finding the condition incurring the reflection.

According to the present invention, the X-ray tube directly irradiates the continuous X-rays onto the crystal, thereby measuring the reflectivity. That is, differently from the conventional method, the present invention directly uses the X-rays irradiated from the X-ray tube when measuring the reflectivity without using the monochromator used for specifying the wavelength of the X-ray.

The X-ray measurement apparatus according to the present invention can simultaneously measure the reflectivity of X-rays with different orders of reflections and include an X-ray tube, a sample-fixing unit and a detector. In addition, the X-ray tube, the sample-fixing unit and the detector are geometrically aligned in the Rowland circle.

The Rowland circle is a circle with a diameter identical to the radius of curvature of a concave grating. The Rowland circle is important for the image forming condition of the concave diffraction grating. The term "Rowland circle" is derived from H. Rowland who first found the concave diffraction grating. In a state that the concave diffraction grating is tangentially aligned with regard to a point positioned in the Rowland circle, if light is incident while aligning an incident slit on a predetermined point of the circle, the spectrum dispersed and image-formed in the concave diffraction grating may be placed on the same circumference.

Those skilled in the art may properly align the X-ray tube, the sample, the detector and other equipment in the Rowland circle in order to achieve the X-ray measurement apparatus of the present invention. That is, the X-ray measurement apparatus according to the present invention has a relatively simple structure so that one can easily construct the X-ray measurement apparatus based on FIG. 1. The precise positions of the X-ray tube and the detector in the Rowland circle can be found by using a conventional method. It is preferred to align parts of the X-ray measurement apparatus under the vacuum state for the purpose of precise measurement. If the Rowland circle has a small size, it is preferred to align the total system in a vacuum container. In this case, it is possible to measure the reflectivity of X-rays having relatively low energy. In contrast, if the Rowland circle has a large size, a size of the X-ray measurement apparatus may be enlarged if the total system is aligned in the vacuum container. Thus, in this case, the vacuum container is provided corresponding to a position of the crystal and the X-ray tube and the detector are connected to the vacuum container through a vacuum pipe, thereby simplifying the fabrication of the system.

Various X-ray tubes known in the art can be used in the present invention. In general, the X-ray is created in X-ray pipes, such as gas pipes or filament pipes. The filament pipes are divided into sealing type filament pipes and exchangeable type filament pipes. In addition, the X-ray tubes are divided into various types according to the kind of metal targets used for the X-ray tubes. The metal targets include Cr, Fe, Co, Cu, Mo, Ag, V, Mn, Fe, Ni, Zr or Rh. The present invention does not limit the kind of the X-ray tubes if they can generate the continuous X-rays.

In addition, the present invention does not limit the kind of the sample-fixing units if they can fix the sample such that the X-rays generated from the X-ray tube can be irradiated onto the sample.

The detector must be equipped with a function of analyzing the reflected waves having various wavelengths. That is, the X-rays reflected from the sample are combination of reflected waves having various wavelengths. Thus, it is necessary for the detector to detect the intensity of each reflected wave in order to measure the reflectivity of the X-rays. For this reason, the detector must have a function of analyzing each reflected wave in order to measure the intensity of reflected waves having different orders of reflections.

Preferably, the detector must have a function of analyzing the reflected X-rays according to wavelengths or energy thereof. The detector includes a fluorescent plate, a photographic film or a counter tube. According to one exemplary embodiment of the present invention, the counter tube is used as the detector. However, it is also possible to use the Si—Li detector or the Si-Pin diode detector without limitation.

The present invention provides the apparatus for simultaneously measuring reflection intensities of X-rays with different orders of reflections including the X-ray tube, the sample-fixing unit and the detector. In addition, the present invention also provides an apparatus for simultaneously measuring integrated reflectivity of X-rays with different orders of reflections by adding a reflectivity calculator to the above reflection measurement apparatus including the X-ray tube, the sample-fixing unit and the detector. The present invention does not limit the kind of the reflectivity calculators if they can calculate the reflectivity based on an intensity ratio of reflected waves to incident waves.

Hereinafter, the present invention will be described in detail with reference to examples and comparative examples of the present invention. The examples and comparative examples of the present invention are illustrative purpose only and they may not intend to limit the scope of the present invention.

EXAMPLE 1

Reflectivity of X-rays in mica is measured by generating X-rays using a copper anode.

Hereinafter, a structure and an operation of the present invention will be described with reference to accompanying drawings.

As shown in FIG. 1, bremsstrahlung generated from an anode of an X-ray tube is irradiated onto a sample crystal (mica) and X-rays reflected from the sample crystal are measured by using a Si—Li detector having an energy resolution function. At this time, the X-ray tube, the sample crystal and the Si—Li detector are geometrically aligned in the Rowland circle.

In detail, the sample crystal (mica crystal) has a size of 70×17 mm and a radius of curvature of 1524 mm. After irradiating the continuous X-rays from the X-ray tube to the mica crystal, the X-rays reflected from the mica crystal are measured by using the Si—Li detector having the energy resolution function available from Ortec Company.

FIG. 2 is a graph illustrating the test result obtained by simultaneously measuring integrated reflectivity of mica crystal when X-rays with 12-orders of reflections are incident into the mica crystal at various Bragg angles (43°, 45°, 47° and 50°). It can be understood from FIG. 2 that energy of the X-rays reflected from the mica crystal is differently represented depending on the Bragg angles.

Figure 3:
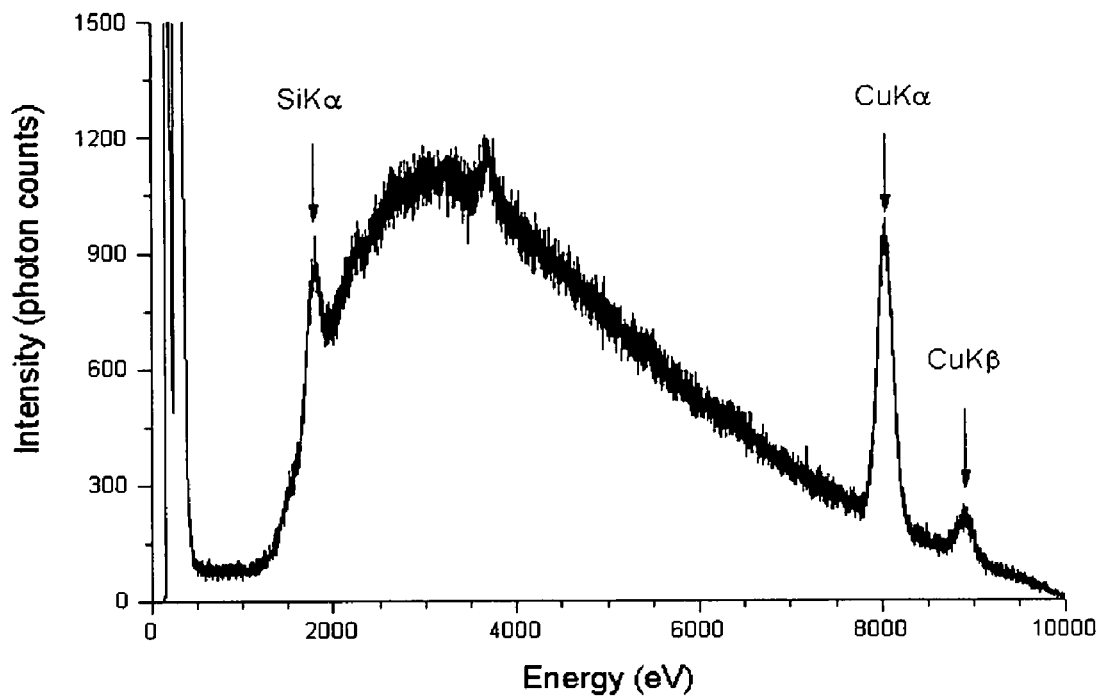
FIG. 3 is a graph illustrating intensity of continuous X-rays generated from an X-ray tube used in the measurement of FIG. 2.

FIG. 3 is a graph illustrating intensity of the continuous X-rays generated from the X-ray tube used in the measurement of FIG. 2. A copper anode is used and FIG. 3 shows a characteristic line and a continuous line of copper. A ratio of a photon count of X-rays reflected from the mica crystal shown in FIG. 2 to a photon count of incident X-rays shown in FIG. 3 is the reflectivity of the X-ray.

The tested reflectivity is shown in Table 1. A unit of the measurement value is "micro rad" and numerical values shown in the brackets are theoretical "kinematic limit" values.

TABLE 1

| Order | 43° | 45° | 47° | 50° |
|---|---|---|---|---|
| 1 | 13.89(13.49) | 20.40(13.59) | 14.28(13.8) | 23.01(14.33) |
| 2 | 3.30(1.39) | 5.07(6.79) | 6.28(10.6) | 11.60(17.20) |
| 3 | 33.40(39.83) | 35.29(39.60) | 36.27(39.9) | 40.47(41.46) |
| 4 | 4.48(5.08) | 5.08(6.33) | 5.8(7.3) | 6.52(7.99) |
| 5 | 22.14(41.38) | 24.04(41.25) | 24.04(40.7) | 26.53(42.28) |
| 6 | 1.23(0.69) | 1.19(0.68) | 1.12(0.7) | 1.19(0.69) |
| 7 | 5.04(5.13) | 5.18(5.16) | 4.77(5.2) | 5.04(5.56) |
| 8 | 8.03(12.95) | 8.96(12.94) | 7.48(12.3) | 8.03(13.80) |
| 9 | 1.12(0.32) | 0.68(0.32) | 0.43(0.3) | 0.53(0.35) |
| 10 | 3.73(3.48) | 2.94(3.47) | 3.06(2.7) | 3.94(3.68) |
| 11 | | 6.17(6.37) | 4.59(4.2) | 25.63(6.75) |
| 12 | | | | 2.88(3.38) |

As can be seen from Table 1, according to the present invention, reflection of X-rays with various orders of reflections can be simultaneously measured in every incident angle. That is, reflection of X-rays with various orders of reflections can be measured at a time. For more precise measurement, the above values can be properly corrected. There is a difference between the measurement values and theoretical values in lower orders because of a beryllium window attached to the detector used in the test. That is, the beryllium window exerts an influence when detecting the X-rays having low energy. This can be easily solved if a vacuum detector is used.

Comparative Example 1

Reflectivity is measured by using the characteristic X-rays according to the conventional method (reference document: G. holzer et al., Physical Scripta 57, 301–309, 1998).

That is, the reflectivity of the characteristic X-rays is measured according to the conventional method disclosed in the above reference document, wherein the reflectivity is measured by using mica crystal identical to that of Example 1 at a Bragg angle of 50° and the test result is compared with that of Example 1. Since comparative example 1 uses the characteristic X-rays, a monochromator crystal is used. In addition, in order to measure the reflectivity of each reflected wave having a predetermined wavelength, the measurement is performed while changing energy for each reflected wave by exchanging an anode of the X-ray tube. Thus, instead of measuring the reflectivity for all reflected waves, reflectivity for predetermined reflected waves has been measured according to the reference document (see, Table 2). In order to measure the reflectivity for each wave having a predetermined wavelength, the total system must be rearranged. The measurement result is shown in Table 2.

TABLE 2

| Order | Comparative Example 1 | Example 1 |
|---|---|---|
| 1 | 13.7 | 23.01 (14.33) |
| 2 | 14.6 | 11.60 (17.20) |
| 3 | 29.8 | 40.47 (41.46) |
| 4 |  | 6.52 (7.99) |
| 5 | 20.0 | 26.53 (42.28) |
| 6 |  | 1.19 (0.69) |
| 7 |  | 5.04 (5.56) |
| 8 | 5.2 | 8.03 (13.80) |
| 9 |  | 0.53 (0.35) |
| 10 |  | 3.94 (3.68) |
| 11 |  | 26.53 (6.75) |
| 12 | 1.2 | 2.88 (3.38) |

As can be seen from Table 2, according to comparative example 1, the system is rearranged by six times while exchanging the anode of the X-ray tube and changing the angle of the monochromator in order to measure 6-orders of reflections. However, according to Example 1, 12-orders of reflections can be measured without rearranging the total system.

INDUSTRIAL APPLICABILITY

As can be seen from the foregoing, according to the present invention, the reflectivity of X-rays with different orders of reflections can be simultaneously measured by using continuous X-rays, so that measurement time can be reduced. In addition, since the reflectivity of X-rays with different orders of reflections can be calculated without rearranging the system, measurement preciseness for the reflectivity can be improved. The method according to the present invention can be used when fabricating or calibrating X-ray spectrometers. In addition, the method according to the present invention can be utilized not only in basic scientific fields, such as fusion plasma analysis, astrophysics or microscopes, but also in various industrial fields.

While this invention has been described in connection with what is presently considered to be the most practical and preferred example, it is to be understood that the invention is not limited to the disclosed embodiment or example and the drawings, but, on the contrary, it is intended to cover various modifications and variations within the spirit and scope of the appended claims.

The invention claimed is:

1. A method of measuring reflectivity by using continuous X-rays, the method comprising:
    irradiating continuous X-rays onto a crystal;
    simultaneously measuring an intensity of various X-rays reflected from the crystal with different orders of reflections;
    calculating reflectivity of the various X-rays reflected from the crystal for each of the different orders of reflections by comparing a reflection intensity of an X-ray detected by a detector with an intensity of the X-ray incident into the crystal, wherein the various X-rays reflected from the crystal satisfy Bragg's Law and constructively interfere;
    and providing the calculated reflectivity.

2. The method according to claim 1, wherein the continuous X-rays are generated by using a metal target selected from the group consisting of Cr, Fe, Co, Cu, Mo, Ag, V, Mn, Fe, Ni, Zr and Rh.

3. The method according to claim 1, wherein the continuous X-rays are generated from an X-ray tube and directly incident into the crystal.

4. The method according to claim 1, wherein the intensity of the continuous X-rays reflected from the crystal is measured through a wavelength analysis method or an energy analysis method.

5. The method according to claim 4, wherein the energy analysis method is preformed by using a Si—Li detector or a Si-Pin diode detector having an energy resolution function.

6. An apparatus for measuring reflectivity of continuous X-rays, the apparatus comprising:
    a continuous X-ray generating X-ray tube;
    a sample-fixing unit;
    a detector having an energy resolution function or a wavelength resolution function; and
    a reflectivity calculator, wherein the X-ray tube, the sample-fixing unit and the detector are geometrically aligned in a Rowland circle, wherein the continuous X-rays generated by the X-ray tube and irradiated onto the sample, and various X-rays satisfying Bragg's Law and constructively interfering are reflected from the sample and arrive at the detector, wherein the detector resolves the various reflected X-rays with different orders of reflections, and wherein the reflectivity calculator simutaneously calculates reflectivities of various reflected X-rays at each of the different orders of reflections by comparing a reflection intensity of an X-ray detected by the detector with an intensity of the X-ray incident into the sample.

7. The apparatus according to claim 6, wherein the X-ray tube uses a metal target including one selected from the group consisting of Cr, Fe, Co, Cu, Mo, Ag, V, Mn, Fe, Ni, Zr and Rh.

8. The apparatus according to claim 6, wherein the X-ray tube includes a gas pipe or a filament pipe.

9. The apparatus according to claim 6, wherein the detector includes a Si—Li detector or a Si-Pin diode detector having an energy resolution function.

* * * * *